US00PP16731P2

(12) United States Plant Patent
Uchneat

(10) Patent No.: US PP16,731 P2
(45) Date of Patent: Jun. 27, 2006

(54) ***PETUNIA* PLANT NAMED 'BALSUNCORA'**

(50) Latin Name: *Petunia hybrida*
Varietal Denomination: Balsuncora

(75) Inventor: Michael S. Uchneat, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 79 days.

(21) Appl. No.: 11/011,532

(22) Filed: Dec. 13, 2004

(51) Int. Cl.
*A01H 5/00* (2006.01)

(52) U.S. Cl. ..... Plt./356
(58) Field of Classification Search ..... Plt./356
See application file for complete search history.

*Primary Examiner*—Anne Marie Grunberg
*Assistant Examiner*—Annette H Para
(74) *Attorney, Agent, or Firm*—Wood, Phillips, Katz, Clark & Mortimer

(57) ABSTRACT

A new and distinct *Petunia* plant named 'Balsuncora' characterized by its salmon-colored flowers, dark green-colored foliage, and vigorous, mounded, and trailing growth habit.

1 Drawing Sheet

Latin name of the genus and species of plant claimed: *Petunia hybrida.*
Variety denomination: 'Balsuncora'.

BACKGROUND OF THE INVENTION

The present invention relates to a new and distinct cultivar of *Petunia* plant botanically known as *Petunia hybrida* and hereinafter referred to by the cultivar name 'Balsuncora'.

The new cultivar originated in a controlled breeding program during November 2001 at Elburn, Ill. The objective of the breeding program was the development of *Petunia* cultivars with single type flowers of unique colors and vigorous, mounded, and trailing growth habits.

The female (seed) parent of 'Balsuncora' was the proprietary *Petunia×hybrida* breeding selection designated 4300-1-1, not patented, characterized by its small, coral-colored flowers. The mate (pollen) parent of 'Balsuncora' was the proprietary *Petunia×hybrida* breeding selection designated 4117-2-1-1, not patented, characterized by its medium sized flowers with yellow-colored throat. The new cultivar was discovered and selected by the inventor as a single flowering plant within the progeny of the above stated cross-pollination during April 2002.

Asexual reproduction of the new cultivar by terminal stem cuttings since April 2002 at Elburn Ill. and West Chicago, Ill., has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balsuncora' as a new and distinct cultivar of *Petunia* plant:

1 Single salmon-colored flowers.

2 Dark green-colored foliage.

3 Freely branching character.

4 Vigorous, mounded, and trailing growth habit.

Plants of the new cultivar differ from plants of the female parent primarily in flower size and from the male parent primarily in flower color and flower size.

Of the many *Petunia* cultivars known to the inventor, the most similar to the new cultivar is the cultivar Kakegawa S57, U.S. Plant Pat. No. 14,007. However, in side-by-side comparisons, flowers of the new cultivar differ from plants of 'Kakegawa S57' in the following characteristics:

1. The flowers of the new cultivar are a different color than the flowers of 'Kakegawa S57'.
2. The plants of the new cultivar have larger flowers than plants of 'Kakegawa S57'.
3. The plants of the new cultivar are not as vigorous as the plants of 'Kakegawa S57'.

BRIEF DESCRIPTION OF THE PHOTOGRAPHS

The accompanying photographs show, as nearly true as it is reasonably possible to make the same in color illustrations of the type, typical flower and foliage characteristics of the new cultivar. Colors in the photographs differ slightly from the color values cited in the detailed description, which accurately describes the colors of 'Balsuncora'. The plants were grown in 10 cm pots for 12 weeks in a greenhouse at West Chicago, Ill.

DETAILED BOTANICAL DESCRIPTION

Figure 1:
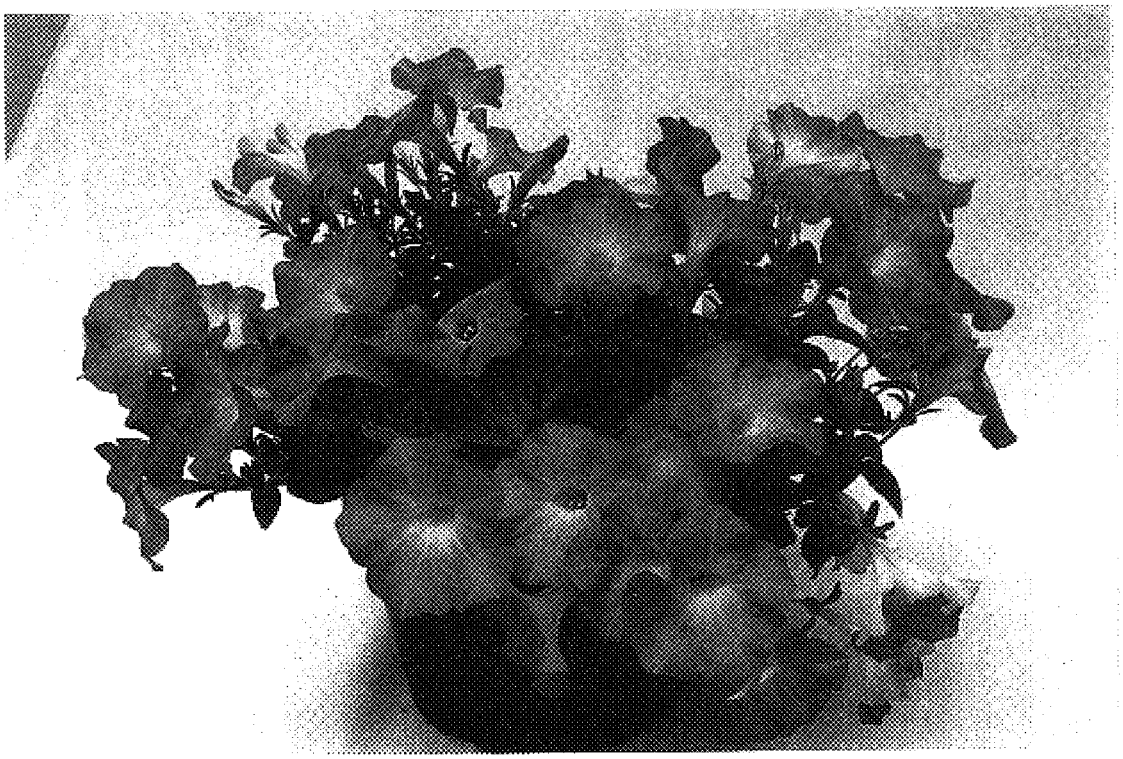
FIG. 1 illustrates a side view of the overall growth and flowering habit of 'Balsuncora'.
Figure 2:
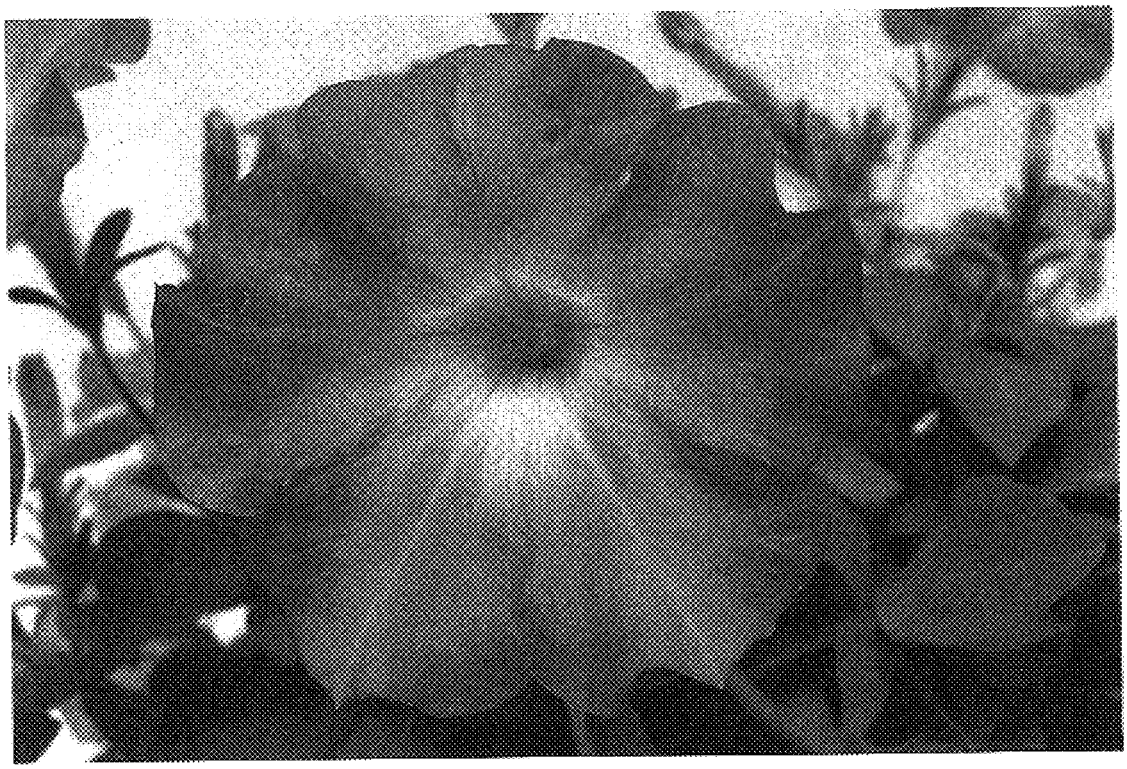
FIG. 2 illustrates a close-up view of a single flower of 'Balsuncora'.

The new cultivar has not been observed under all possible environmental conditions to date. Accordingly, it is possible that the phenotype may vary somewhat with variations in the environment, such as temperature, light intensity, and day length without, however, any variation in genotype.

The chart used in the identification of colors described herein is The R.H.S. Colour Chart of The Royal Horticultural Society, London, England, 2001 edition, except where general color terms of ordinary significance are used. The color values were determined on Oct. 15, 2004 between 1:00 and 3:00 p.m. under natural daylight conditions.

The following descriptions and measurements describe plants produced from cuttings taken from stock plants and grown in a double polycarbonate-covered greenhouse under conditions comparable to those used in commercial practice. The plants were grown in 10 cm pots for 12 weeks utilizing a soil-less growth medium. Greenhouse temperatures were maintained at approximately 55°–75° F. (13°–24° C.) during the day and approximately 50°–60° F. (10°–16° C.) during the night. Greenhouse light levels were maintained at approximately 5,000–8,000 footcandles during the day.

Botanical classification: *Petunia×hybrida* cultivar Balsuncora.

Parentage:

*Female (seed) parent*.—Proprietary *Petunia×hybrida* breeding selection designated 4300-1-1, not patented.

*Male (pollen) parent*.—Proprietary *Petunia×hybrida* breeding selection designated 4117-2-1-1, not patented.

Propagation:

*Type cutting*.—Terminal stem.

*Time to initiate roots*.—Approximately 6 to 9 days.

*Time to produce a rooted cutting*.—Approximately 21 to 30 days.

*Root description*.—Fibrous.

*Rooting habit*.—Freely branching.

Plant description:

*Crop time*.—Approximately 6 to 8 weeks are required to produce a finished plant from rooted cuttings.

*Habit of growth*.—Vigorous and freely branching. Pinching improves basal branching.

*Form*.—Initially upright, becoming mounded and cascading as it matures.

*Size*.—Height from soil level to top of plant plane: Approximately 14 cm from top of soil to top of plant plane. Diameter (area of spread) — Approximately 36 cm.

*Lateral branches*.—Quantity: An average of 3 branches per plant develop after pinching. Strength: Strong. Length: Approximately 26 cm. Diameter: Approximately 2.4 mm. Texture: Villous. Color: 144A. Internode length at the middle of the branch: Approximately 1.5 cm.

*Foliage*.—Quantity per lateral branch: Approximately 29. Type: Simple. Arrangement on flowering stem: Opposite. Angle to stem: Acute. Shape: Ovate. Margin: Entire. Apex: Acute. Base: Attenuate. Venation pattern: Pinnate. Leaf length: Approximately 4.3 cm. Leaf width: Approximately 3.1 cm. Texture: Upper and lower surfaces: Dense, stipulate glandular. Color of upper surface of mature foliage: Closest to 137A with venation closest to 143C. Color of lower surface of mature foliage: Closest to 137C with venation closest to 143C. Petiole length: Approximately 3 mm. Petiole diameter: Approximately 2 mm. Petiole texture: Villous. Petiole color: Closest to 143C.

Flowering description:

*Flowering habit*.—Freely flowering under outdoor growing conditions with substantially continuous blooming from spring through autumn and year round in greenhouse environment.

*Quantity of flowers*.—Approximately 12 fully open flowers per plant.

*Lastingness of individual bloom*.—Approximately 4–5 days.

Flower description:

*Type*.—Single, solitary, salverform, indeterminate and persistent. Fragrance: Pungent.

*Size*.—Length (height): Approximately 5.5 cm. Diameter: Approximately 6.2 cm.

*Flower bud*.—Rate of opening: Generally takes 2–3 days for bud to progress from first color to fully open flower. Shape: Oblong. Length at first color: Approximately 4 cm. Diameter at tip at first color: Approximately 1 cm. Diameter at base at first color: Approximately 4 mm. Texture: Villous. Color: 56C.

*Corolla*.—Approximately 5 petals fused to form corolla tube. Petal shape: Obovate. Petal apex: Cuspidate. Petal margin: Entire. Petal length from throat: 2.5 cm. Petal width at widest point: 3.3 cm. Petal texture: Glabrous. Color of upper surface when fully open: Closest to 51A at margin gradually fading to 56D at throat with venation of 144C. Color of lower surface when fully open: 56A at margin gradually fading to 155A at throat with venation of 144C.

*Corolla tube*.—Length: Approximately 3.3 cm. Diameter at distal end: Approximately 1 cm. Diameter at proximal end: Approximately 5 mm. Texture: Outer surface: Villous. Inner surface: Glabrous. Color of outer surface: Closest to 151C with venation of 144C. Color of inner surface: Closest to 153C with venation of 144C.

*Peduncle*.—Strength: Strong. Angle to the stem: Acute. Length: Approximately 2.7 cm. Diameter: Approximately 1.8 mm. Texture: Villous. Color: Closest to 144A.

*Calyx*.—Formed by five, non-imbricate sepals, fused at base. Sepal shape: Linear. Sepal apex: Obtuse. Sepal margin: Entire. Length: Approximately 1.8 cm. Width: Approximately 3 mm. Texture of both surfaces: Villous. Color of upper surface: 137A. Color of lower surface: 137C.

*Reproductive organs*.—Stamen quantity: Approximately 5. Stamen length: Approximately 2.5 cm. Filament length: Approximately 1.6 cm. Filament color: 155C. Anther shape: Oval, bi-lobed. Anther length: Approximately 1 mm. Anther color: 155B. Pollen amount: Abundant. Pollen color: Lighter than 8D. Pistil quantity: 1 per flower. Pistil length: Approximately 2.6 cm. Stigma shape: Funnel. Stigma length: Approximatey 2 mm. Stigma color: 145B. Style length: Approximately 2.1 cm. Style color: 144C. Ovary size: Approximately 3 mm. Ovary color: 144A.

Seed and fruit production: Neither seed nor fruit production has been observed.

Disease and pest resistance: Resistance to pathogens and pests common to *petunias* has not been observed.

What is claimed is:

1. A new and distinct cultivar of *Petunia* plant named 'Balsuncora,' substantially as herein shown and described.

* * * * *